(12) United States Patent
Tsukuda et al.

(10) Patent No.: US 9,108,049 B2
(45) Date of Patent: Aug. 18, 2015

(54) CONTROL UNIT OF RADIOTHERAPY APPARATUS AND RADIOTHERAPY APPARATUS CONTROLLING METHOD

(75) Inventors: Kazuhiro Tsukuda, Tokyo (JP); Shuji Kaneko, Tokyo (JP); Takumi Kawamitsu, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 133 days.

(21) Appl. No.: 13/813,742

(22) PCT Filed: Apr. 25, 2011

(86) PCT No.: PCT/JP2011/060048
§ 371 (c)(1),
(2), (4) Date: Feb. 1, 2013

(87) PCT Pub. No.: WO2012/026160
PCT Pub. Date: Mar. 1, 2012

(65) Prior Publication Data
US 2013/0131431 A1    May 23, 2013

(30) Foreign Application Priority Data
Aug. 26, 2010    (JP) .................................. 2010-189754

(51) Int. Cl.
*A61N 5/10*    (2006.01)

(52) U.S. Cl.
CPC ............ *A61N 5/1064* (2013.01); *A61N 5/1049* (2013.01); *A61N 2005/1061* (2013.01)

(58) Field of Classification Search
CPC .................... A61N 2005/1061; A61N 5/1049; A61N 5/1064
USPC ............................ 600/1, 407, 427; 378/41, 65
See application file for complete search history.

(56) References Cited

U.S. PATENT DOCUMENTS

| 7,227,925 B1* | 6/2007 | Mansfield et al. ............... 378/65 |
| 7,239,684 B2* | 7/2007 | Hara et al. ...................... 378/65 |

(Continued)

FOREIGN PATENT DOCUMENTS

| CN | 1373644 A | 10/2002 |
| GB | 2 353 458 | 2/2001 |

(Continued)

OTHER PUBLICATIONS

International Preliminary Report on Patentability and Written Opinion of the International Searching Authority issued Mar. 19, 2013 in International (PCT) Application No. PCT/JP2011/060048.

(Continued)

*Primary Examiner* — Baisakhi Roy
(74) *Attorney, Agent, or Firm* — Wenderoth, Lind & Ponack, L.L.P.

(57) ABSTRACT

A radiotherapy apparatus controlling method according to the present invention includes controlling an imager driving unit to move an imaging unit to a position, and to image a transmission image by the imaging unit based on a radiation emitted from a first irradiating unit; and controlling the imager driving unit to move the imaging unit to a position, and to image a transmission image based on a radiation emitted from a second irradiating unit. According to such a radiotherapy apparatus controlling method, it is not necessary to separately provide an imaging unit which images the transmission image using a first radiation emitted from the first irradiating unit and an imaging unit which images a transmission image from the radiation emitted from the second irradiating unit, and a radiotherapy apparatus can be manufactured to be cheaper.

12 Claims, 6 Drawing Sheets

(56) References Cited

U.S. PATENT DOCUMENTS

| | | |
|---|---|---|
| 2004/0024300 A1 | 2/2004 | Graf |
| 2004/0068169 A1 | 4/2004 | Mansfield et al. |
| 2007/0140425 A1 | 6/2007 | Kamikonya et al. |
| 2008/0197304 A1 | 8/2008 | Urano et al. |
| 2008/0279339 A1 | 11/2008 | Fadler |
| 2009/0296886 A1 | 12/2009 | Maltz et al. |
| 2010/0020931 A1 | 1/2010 | Otto et al. |
| 2012/0123184 A1* | 5/2012 | Otto et al. .................. 600/1 |

FOREIGN PATENT DOCUMENTS

| | | |
|---|---|---|
| JP | 11-76435 | 3/1999 |
| JP | 2003-506187 | 2/2003 |
| JP | 2003-522576 | 7/2003 |
| JP | 2006-501933 | 1/2006 |
| JP | 3785136 | 6/2006 |
| JP | 2007-130448 | 5/2007 |
| JP | 2008-200090 | 9/2008 |
| WO | 01/12066 A2 | 2/2001 |

OTHER PUBLICATIONS

International Search Report issued Aug. 9, 2011 in International (PCT) Application No. PCT/JP2011/060048.

Yuichiro Kamino et al., "Development of a Four-Dimensional Image-Guided Radiotherapy System with a Gimbaled X-Ray Head", (Int. J. Radiation Oncology Biol. Phys., vol. 66, No. 1, pp. 271-278, 2006).

Extended European Search Report issued Jan. 30, 2014 in corresponding European Patent Application No. 11819635.1.

Chinese Office Action issued Nov. 13, 2014, in corresponding Chinese Application No. 201180039388.0 (with partial English translation).

* cited by examiner

CONTROL UNIT OF RADIOTHERAPY APPARATUS AND RADIOTHERAPY APPARATUS CONTROLLING METHOD

TECHNICAL FIELD

The present invention relates to a control unit of a radiotherapy apparatus and a radiotherapy apparatus controlling method, and more particularly, relates to a control unit of a radiotherapy apparatus and a radiotherapy apparatus controlling method, which control a radiotherapy apparatus used when a tumor affected region inside a human body is treated with radiation.

BACKGROUND ART

A CBCT (Cone Beam Computed Tomography) is known which reconstructs a three-dimensional CT data of an imaging target on the basis of a plurality of transmission images imaged by using a cone X-ray irradiated to the imaging target from a radiation source which is turned around the imaging target. In such a CBCT, the three-dimensional CT data can be prepared in a short time without turning the radiation source a plurality of times. It is desired to prepare the three-dimensional CT data that exhibits a more suitable view field.

A radiotherapy is known in which a patient is treated by irradiating therapeutic radiation to a tumor affected region. A radiotherapy apparatus contains an imager system for imaging transmission images of the patient lying on a couch; and a therapeutic radiation irradiating unit for irradiating the therapeutic radiation to the patient. The radiotherapy apparatus is desired to be cheaper in manufacturing cost and longer in life.

"DEVELOPMENT OF A FOUR-DIMENSIONAL IMAGE-GUIDED RADIOTHERAPY SYSTEM WITH A GIMBALED X-RAY HEAD" discloses a technique of checking a position of tumor with a therapeutic beam by use of EPID (Electronic Portal Imaging Device).

In JP 2003-522576A, a cone beam computer tomography system is disclosed which contains a flat panel imager for imaging transmission images by using an X-ray beam which has transmitted through the object while turning around an object, and reconstructs a three-dimensional CT data on the basis of the transmission images. The cone beam computer tomography system can change the size of a view field of the three-dimensional CT data by changing a position of the flat panel imager with respect to an X-ray source that emits the X-ray beam.

Japanese Patent No. 3,785,136 discloses a radiotherapy apparatus that can easily design a therapy plan after the radiotherapy is performed on a specimen. The radiotherapy apparatus contains a radiation irradiating head for irradiating therapeutic radiation; an image processing section for generating an image of an affected region of the specimen to which the therapeutic radiation is irradiated from the radiation irradiation head; and a control unit for controlling the radiation irradiating head and the image processing section so that a period is repeated which includes the generation for the image and irradiation of the therapeutic radiation, and prior to the irradiation of the therapeutic radiation in a first period, the imaging of the image is completed in which a diagnostic X-ray in a second period next to the first period is used, and processing of the imaged image is completed in the irradiation of the therapeutic radiation in the first period, and the image of the affected region is generated.

CITATION LIST

[Patent Literature 1] JP 2003-522576A
[Patent Literature 2] Japanese Patent No. 3785136
[Non-Patent Literature 1] "DEVELOPMENT OF A FOUR-DIMENSIONAL IMAGE-GUIDED RADIOTHERAPY SYSTEM WITH A GIMBALED X-RAY HEAD" (Int. J. Radiation Oncology Biol. Phys., Vol. 66, No. 1, pp. 271-278, 2006) by Kamino Y, Takayama K, Kokubo M, et al.

SUMMARY OF THE INVENTION

An object of the present invention is to provide a control unit of a radiotherapy apparatus and a radiotherapy apparatus controlling method, in which a manufacturing cost of the radiotherapy apparatus can be reduced.

Another object of the present invention is to provide a control unit of a radiotherapy apparatus and a radiotherapy apparatus controlling method, in which three-dimensional data in an appropriate view field can be reconstructed.

Another object of the present invention is to provide a control unit of a radiotherapy apparatus and a radiotherapy apparatus controlling method, in which the lifetime of the radiotherapy apparatus can be extended.

The radiotherapy apparatus control unit according to the present invention is provided with a first imaging section configured to control an imager driving unit to move an imaging unit to a gantry such that the imaging unit is positioned into a first position; and a second imaging section configured to control the imager driving unit such that the imaging unit is positioned into a second position. The imaging unit receives a first transmission radiation, which has transmitted through a predetermined region, of a first radiation emitted from a first irradiating unit supported by the gantry, when the imaging unit is positioned into the first position, and images a first transmission image from the first transmission radiation. When the imaging unit is positioned into the second position, the imaging unit receives a second transmission radiation, which has transmitted through a predetermined region, of a second radiation emitted from a second irradiating unit supported by the gantry, and images a second transmission image from the second transmission radiation. According to such a control unit of a radiotherapy apparatus, the imaging unit which images the transmission image from the second radiation irradiated from the second irradiating unit and the imaging unit which images the transmission image from the first radiation irradiated from the first irradiating unit do not need to be separately or independently provided in the radiotherapy apparatus. As a result, it is possible to manufacture it cheaper.

The control unit of the radiotherapy apparatus according to the present invention is further provided with a first reconstruction image imaging section configured to control the imager driving unit to move the imaging unit such that the imaging unit is positioned into a first reorganization position to the gantry; a first reconstructing section configured to configure first three-dimensional data based on a plurality of the first transmission images imaged from the first radiation by the imaging unit when the imaging unit is positioned into the first reconstruction position; a second reconstruction image imaging section configured to control the imager driving unit to move the imaging unit such that the imaging unit is positioned into a second reconstruction position to the gantry; and a second reconstructing section configured to reconstruct second three-dimensional data based on a plurality of the second transmission images imaged by the imaging unit when the imaging unit is positioned into the second reconstruction position. The gantry rotates around a rotation axis to a ring. The plurality of first reconstruction transmission images are imaged when the gantry is positioned into a plurality of first gantry angles different from each other to the ring. The plurality of second reconstruction transmission images are imaged when the gantry is positioned into a plurality of second gantry angles different from each other to the ring. A first reconstruction position and a second reconstruction position are set such that a position in which the rotation axis is reflected on the plurality of first reconstruction transmission images is different from a position in which the rotation axis is reflected on the plurality of second reconstruction transmission images. Such a control unit of the radiotherapy apparatus, the view field of the second three-dimensional data can be made wider than the view field of the first three-dimensional data by appropriately setting the first reconstruction position and the second reconstruction position. The time period taken to image the plurality of first reconstruction transmission images can be reduced to be shorter than the time period taken to image the plurality of second reconstruction transmission images. In such a control unit of the radiotherapy apparatus, both of the first three-dimensional data and the second three-dimensional data can be generated and only one selected appropriately from the first three-dimensional data and the second three-dimensional data may be generated.

The imager driving unit includes a circumferential direction driving unit configured to drive the imaging unit to turn around the rotation axis to the gantry; and a radial direction driving unit configured to drive the imaging unit to move in parallel to a radial direction orthogonal to the rotation axis to the gantry. According to such a control unit of the radiotherapy apparatus, even when an appropriate position in a radial direction for imaging from the second radiation irradiated from the second irradiating unit is different from an appropriate position in the radial direction for imaging from the first radiation irradiated from the first irradiating unit, the imaging unit can be positioned into a position appropriate for the imaging and the transmission image can be more appropriately imaged.

The control unit of the radiotherapy apparatus according to the present invention is further provided with a radiotherapy section configured to control the second irradiating unit to irradiate a therapeutic radiation to a specimen. The radiotherapy section controls the imager driving unit such that the imaging unit is positioned into an avoidance position, when the therapeutic radiation is irradiated to the specimen. The avoidance position is set such that a dose of the therapeutic radiation to which the imaging unit is exposed when the imaging unit is positioned into the avoidance position is smaller than a dose of the therapeutic radiation to which the imaging unit is exposed when the imaging unit is positioned into the second position. In the control unit of the radiotherapy apparatus, an exposure dose of the therapeutic radiation by the imaging unit can reduced and the lifetime of such an imaging unit can be extended.

The control unit of the radiotherapy apparatus according to the present invention is further provided with a stereoscopic view imaging section configured to control another imaging unit supported by the gantry such that a third transmission image is imaged from a radiation portion which has transmitted through a predetermined region, of a radiation emitted from a third irradiating unit supported by the gantry. The radiotherapy section controls a gimbal unit which moves the second irradiating unit to the gantry, based on a first stereoscopic view image imaged by the imaging unit when the imaging unit is positioned into the first position, and a second stereoscopic view image imaged by the other imaging unit. The radiotherapy section controls the gimbal unit to move the second imaging unit to the gantry based on the first stereoscopic view image imaged by the imaging unit and the second stereoscopic view image imaged by another imaging unit, when the imaging unit is positioned in the first position. According to such a control unit of the radiotherapy apparatus, the first stereoscopic view image and the second stereoscopic view image which are imaged from two directions which are different each other can be imaged at substantially a same time. Therefore, according to such a control unit of the radiotherapy apparatus, the position of the moving portion in a specimen can be calculated in a higher accuracy based on the first stereoscopic view image and the second stereoscopic view image and the therapeutic radiation can be irradiated to the portion in a higher accuracy.

A radiotherapy apparatus controlling method according to the present invention includes controlling an imager driving unit to move an imaging unit to a gantry, such that the imaging unit which images a transmission image by receiving a radiation is positioned into a first position, before a first radiation is emitted from a first irradiating unit supported by the gantry; and controlling the imager driving unit such that the imaging unit is positioned into a second position, before a second radiation is emitted from a second irradiating unit supported by the gantry. A first transmission radiation which has transmitted through a predetermined region, of the first radiation is received by the imaging unit when the imaging unit is positioned into the first position. A second transmission radiation which has transmitted through a predetermined region, of the second radiation is received by the imaging unit when the imaging unit is positioned into the second position. According to such a radiotherapy apparatus controlling method, the radiotherapy apparatus does not have to be separately provided with the imaging unit which images a transmission image from the second radiation irradiated from the second irradiating unit and the imaging unit which images a transmission image from the first radiation irradiated from the first irradiating unit. The radiotherapy apparatus can be manufactured to be cheaper.

The radiotherapy apparatus controlling method according to the present invention is further provided with rotating the gantry around a rotation axis to a ring; controlling the imager driving unit to drive the imaging unit to be positioned into a first reconstruction position to the gantry; reconstructing first three-dimensional data based on a plurality of first reconstruction transmission images imaged from a radiation emitted from the first irradiating unit when the imaging unit is positioned into a first reconstruction position; controlling the imager driving unit to drive the imaging unit to be positioned into a second reconstruction position to the gantry; and reconstructing second three-dimensional data based on a plurality of second reconstruction transmission images imaged from the radiation emitted from the second irradiating unit when the imaging unit is positioned into the second reconstruction position. The plurality of first reconstruction transmission images are images imaged when the gantry is positioned into a plurality of first gantry angles different from each other to the ring. The plurality of second reconstruction transmission images are images imaged when the gantry is positioned into a plurality of second gantry angles different from each other to the ring. The first reconstruction position and the first reconstruction position are set such that a position on which the rotation axis is reflected on the plurality of first reconstruction transmission images is different from a position on which the rotation axis is reflected on the plurality of second reconstruction transmission images. According to such a radiotherapy apparatus controlling method, by appropriately setting the first reconstruction position and the second reconstruction position, the view field of the second three-dimensional data can be made larger than the view field of the first three-dimensional data, and a time required to image the plurality of first reconstruction transmission images can be reduced shorter than a time required to image the plurality of second reconstruction transmission images. According to such a radiotherapy apparatus controlling method, both of the first three-dimensional data and the second three-dimensional data can be generated and only one of the first three-dimensional data and the second three-dimensional data can be appropriately selected.

The imager driving unit is provided with a circumferential direction driving unit configured to drive the imaging unit to turn around the rotation axis to the gantry; and a radial direction driving unit configured to drive the imaging unit to move in parallel to a radial direction which is orthogonal to the rotation axis to the gantry. According to such a radiotherapy apparatus controlling method, even when an appropriate position in a radial direction for imaging by the imaging unit using the radiation irradiated from the therapy irradiating unit is different from an appropriate position in the radial direction for imaging by the imaging unit using the diagnostic radiation, the imaging unit can be positioned into the appropriate position, and the transmission image can be imaged more appropriately.

The radiotherapy apparatus controlling method according to the present invention is further provided with controlling the imager driving unit to move the imaging unit to an avoidance position to the gantry, before the second irradiating unit irradiates a therapeutic radiation. The avoidance position is set such that a radiation dose of the therapeutic radiation by the imaging unit when the imaging unit is positioned into the avoidance position is smaller than that of the therapeutic radiation by the imaging unit when the imaging unit is positioned into the second position. In such a radiotherapy apparatus controlling method, the exposure dose of the radiation of the imaging unit can be reduced, and the lifetime of the imaging unit can be extended.

The radiotherapy apparatus controlling method of the present invention further includes: calculating an irradiation position based on a first stereoscopic view image and a second stereoscopic view image; and controlling a gimbal unit which moves the second irradiating unit to the gantry, based on the irradiation region, before the therapeutic radiation is irradiated. The gantry further supports: a third irradiating unit configured to irradiate a third radiation; and another imaging unit configured to image a transmission image by receiving which has transmitted through a predetermined region of the third radiation. The first stereoscopic view image is the transmission image imaged by the imaging unit when the imaging unit is positioned into the first position. The second stereoscopic view image is the transmission image imaged by the other imaging unit. According to such a radiotherapy apparatus controlling method, the first stereoscopic view image and the second stereoscopic view image can be imaged from the two directions different from each other at almost a same time. Therefore, according to such a radiotherapy apparatus controlling method, the position of a moving portion of a specimen can be calculated in a higher accuracy based on the first stereoscopic view image and the second stereoscopic view image, and the therapeutic radiation can be irradiated to the portion in a higher accuracy.

A computer-readable recording medium of the present invention stores a computer program to make a computer execute the radiotherapy apparatus controlling method of the present invention.

A control unit of a radiotherapy apparatus according to the present invention is provided with a radiotherapy section configured to control a therapeutic irradiating unit such that the therapeutic irradiating unit irradiates a therapeutic radiation to a predetermined region; and an imaging section configured to control an imager driving unit to move an imaging unit such that the imaging unit is positioned into an imaging position, when the therapeutic irradiating unit irradiates an imaging radiation to a predetermined region. The radiotherapy section controls the imager driving unit such that the imaging unit is positioned into an avoidance position, when the therapeutic radiation is irradiated. The imaging unit receives the transmission radiation which has transmitted through the predetermined region, of an imaging radiation when the imaging unit is positioned into the imaging position and images the transmission image from the transmission radiation. The avoidance position is set such that a radiation dose of the therapeutic radiation by the imaging unit when the imaging unit is positioned into the avoidance position is smaller than that of the therapeutic radiation by the imaging unit when the imaging unit is positioned into the imaging position. In such a radiotherapy apparatus control unit, the radiation dose of the therapeutic radiation by the imaging unit can be reduced to lower level than a case where the imaging unit is positioned in the imaging position, when the therapeutic radiation is irradiated. Thus, the lifetime of the imaging unit can be extended.

A radiotherapy apparatus controlling method of the present invention includes controlling an imager driving unit to move an imaging unit such that the imaging unit is positioned into an imaging position, before a therapeutic irradiating unit irradiates to a predetermined region; and controlling the imager driving unit to move the imaging unit to an avoidance position, before the therapeutic irradiating unit irradiates the therapeutic radiation to a predetermined region. The imaging unit receives a transmission radiation, which has transmitted through a predetermined position, of an imaging radiation when the imaging unit is positioned into the imaging position and images a transmission image from the transmission radiation. The avoidance position is set such that a radiation dose of the therapeutic radiation by the imaging unit when the imaging unit is positioned into the avoidance position is smaller than that of the therapeutic radiation by the imaging unit when the imaging unit is positioned into the imaging position. According to such a radiotherapy apparatus controlling method, an exposure dose of the therapeutic radiation by the imaging unit can be reduced to a lower level than that of the therapeutic radiation by the imaging unit in case of the imaging unit positioned into the imaging position, when the therapeutic radiation is irradiated. Thus, the lifetime of the imaging unit can be extended.

According to the control unit of the radiotherapy apparatus and the radiotherapy apparatus controlling method in the present invention, the radiotherapy apparatus does not need to be separately provided with two imaging units corresponding to two irradiating unit, and can be cheaper manufactured.

DESCRIPTION OF EMBODIMENTS

Figure 1:
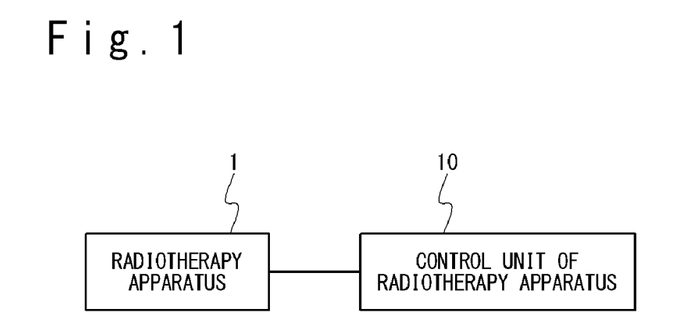
FIG. 1 is a block diagram showing a radiotherapy system.

Hereinafter, a control unit of a radiotherapy apparatus according to embodiments of the present invention will be described with reference to the attached drawings. The control unit 10 is applied to a radiotherapy system, as shown in FIG. 1. The radiotherapy system contains the radiotherapy apparatus 1 and the control unit 10. The control unit 10 is connected to the radiotherapy apparatus 1 so that data can be transmitted bi-directionally.

Figure 2:
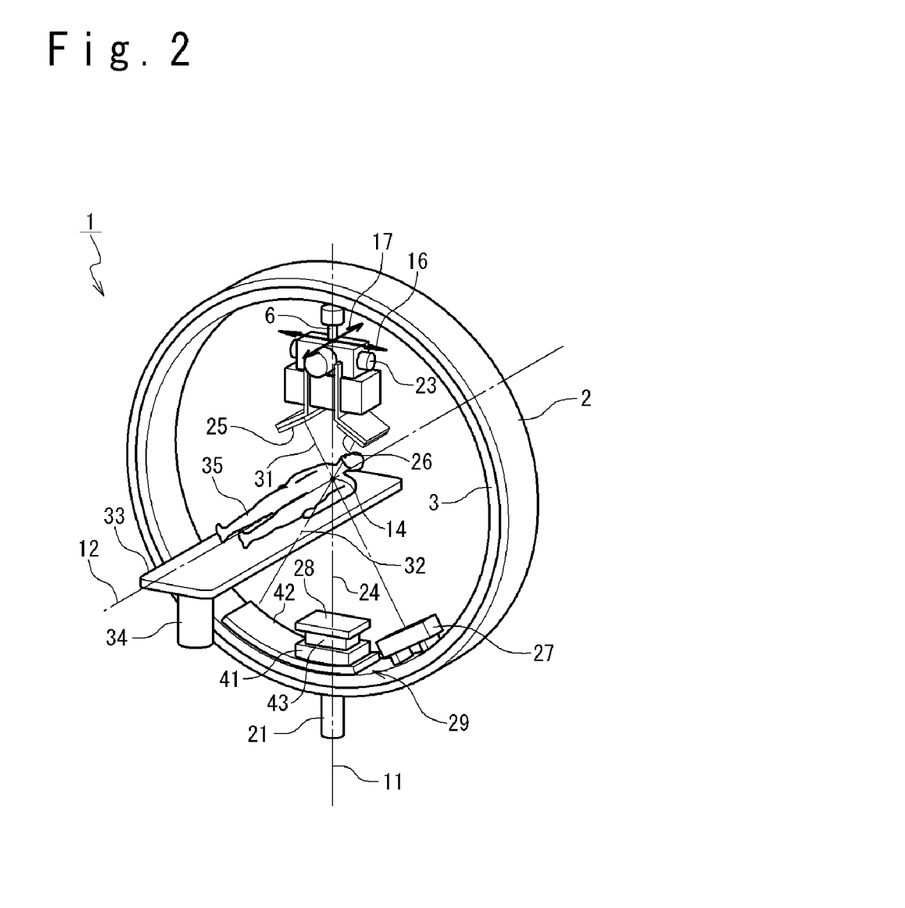
FIG. 2 is a perspective view showing a radiotherapy apparatus.

The radiotherapy apparatus 1 contains an O-ring 2, a running gantry 3 and a radiation irradiating unit 6. The O-ring 2 is ring-shaped and supported on a base so that the O-ring 2 can be rotated around a ring rotation axis 11. The ring rotation axis 11 is parallel to a vertical direction. The running gantry 3 is ring-shaped. The running gantry 3 is arranged inside the O-ring 2 and supported by the O-ring 2 so that the running gantry 3 can be rotated around a gantry rotation axis 12. The gantry rotation axis 12 is orthogonal to the vertical direction and intersects the ring rotation axis 11 at an isocenter 14. The gantry rotation axis 12 is fixed to the O-ring 2. That is, the gantry rotation axis 12 is rotated around the ring rotation axis 11 together with the O-ring 2.

The radiation irradiating unit 6 is arranged inside the ring of the running gantry 3. The radiation irradiating unit 6 is supported by the running gantry 3 so that the radiation irradiating unit 6 is turnable around a tilt axis 16 and turnable around a pan axis 17. The tilt axis 16 is orthogonal to the pan axis 17. The intersection of the tilt axis 16 and the pan axis 17 is away from the isocenter 14 by one meter. The radiation irradiating unit 6 is controlled by the control unit 10 to emit a therapeutic radiation 24 whose irradiation field is controlled. As the therapeutic radiation 24, an MV-X ray is exemplified which is generated by a bremsstrahlung radiation of an electron beam accelerated with acceleration voltage of 8 MV. The therapeutic radiation 24 is a conically-shaped cone beam which is emitted from a virtual point source of the radiation irradiating unit 6 and which has the virtual point source as an apex. The virtual point source is positioned at the intersection of the tilt axis 16 and the pan axis 17.

The radiotherapy apparatus 1 further contains a ring driving unit 21 and a gimbal unit 23 and contains a gantry driving unit (not shown). The ring driving unit 21 is controlled by the control unit 10 and rotates the O-ring 2 around the ring rotation axis 11. The ring driving unit 21 further measures a ring angle at which the O-ring 2 is positioned with respect to the base and outputs the ring angle to the control unit 10. The gantry driving unit is controlled by the control unit 10 and rotates the running gantry 3 around the gantry rotation axis 12. The gantry driving unit further measures a gantry angle at which the running gantry 3 is positioned with respect to the O-ring 2 and outputs the gantry angle to the control unit 10.

The gimbal unit 23 is controlled by the control unit 10 and turns the radiation irradiating unit 6 around the tilt axis 16 and turns the radiation irradiating unit 6 around the pan axis 17. The gimbal unit 23 further measures a tilt angle at which the radiation irradiating unit 6 is turned around the tilt axis 16 with respect to the running gantry 3 and outputs the tilt angle to the control unit 10. The gimbal unit 23 further measures a pan angle at which the radiation irradiating unit 6 is turned around the pan axis 17 with respect to the running gantry 3 and outputs the pan angle to the control unit 10.

The radiation irradiating unit 6 is supported by the running gantry 3, as mentioned above. Thus, once the radiation irradiating unit 6 is fixed to the running gantry 3 to be oriented to the isocenter 14, the therapeutic radiation 24 is always outputted to the isocenter 14, even if the O-ring 2 is rotated by the ring driving unit 21 or even if the running gantry 3 is rotated by the gantry driving unit. That is, the radiotherapy apparatus 1 can irradiate the therapeutic radiation 24 from an optional direction to the isocenter 14 through the running and turning operations.

The radiotherapy apparatus 1 further contains a plurality of imager systems. That is, the radiotherapy apparatus 1 contains a first diagnostic radiation irradiating unit 25, a second diagnostic radiation irradiating unit 26, a first imaging unit 27, a second imaging unit 28 and an imager driving unit 29. The first diagnostic radiation irradiating unit 25 is supported by the running gantry 3 and arranged inside the ring of the running gantry 3 so that an angle between a line linking the isocenter 14 and the first diagnostic radiation irradiating unit 25 and a line linking the isocenter 14 and the radiation irradiating unit 6 is acute. The second diagnostic radiation irradiating unit 26 is supported by the running gantry 3 and arranged inside the ring of the running gantry 3 so that an angle between a line linking the isocenter 14 and the second diagnostic radiation irradiating unit 26 and a line linking the isocenter 14 and the radiation irradiating unit 6 is acute. The second diagnostic radiation irradiating unit 26 is further arranged so that an angle between a line linking the isocenter 14 and the first diagnostic radiation irradiating unit 25 and a line linking the isocenter 14 and the second diagnostic radiation irradiating unit 26 is a right angle (90 degrees).

The first diagnostic radiation irradiating unit 25 is controlled by the control unit 10 and emits a first diagnostic radiation 31 to the isocenter 14 at a predetermined timing. As the first diagnostic radiation 31, a kV-X ray is exemplified which is generated by the bremsstrahlung radiation of the electron beam accelerated with the acceleration voltage of 100 kV. The first diagnostic radiation 31 is outputted from the virtual point source of the first diagnostic radiation irradiating unit 25 and is a conically-shaped cone beam which has the virtual point source as an apex. The second diagnostic radiation irradiating unit 26 is controlled by the control unit 10 and outputs a second diagnostic radiation 32 to the isocenter 14 at a predetermined timing. As the second diagnostic radiation 32, the kV-X ray is exemplified which is generated by the bremsstrahlung radiation of the electron beam accelerated with the acceleration voltage of 100 kV. The second diagnostic radiation 32 is outputted from the virtual point source of the second diagnostic radiation irradiating unit 26 and is the conically-shaped cone beam which has the virtual point source as an apex.

The first imaging unit 27 is supported by the running gantry 3 and arranged to oppose to the first diagnostic radiation irradiating unit 25 through the isocenter 14. The second imaging unit 28 is supported movably to the running gantry 3. The imager driving unit 29 is controlled by the control unit 10 and moves the second imaging unit 28 with respect to the running gantry 3.

The first imaging unit 27 contains a light receiving section. The first imaging unit 27 is controlled by the control unit 10 and generates a first transmission image on the basis of the X-ray received by the light receiving section. As the first imaging unit 27, FPD (Flat Panel Detector) and X-ray II (Image Intensifier) are exemplified. The second imaging unit 28 contains a light receiving section. The second imaging unit 28 is controlled by the control unit 10 and generates a second transmission image on the basis of the X-ray received by the light receiving section. As the second imaging unit 28, EPID (Electronic Portal Imaging Device), FPD (Flat Panel Detector) and X-ray II (Image Intensifier) are exemplified. The transmission image is formed from a plurality of pixels. The plurality of pixels are arranged in the shape of a matrix on the transmission image and related to respective brightnesses. A photographic subject is reflected on the transmission image because each of the plurality of pixels is colored based on the brightness of the pixel.

The radiotherapy apparatus 1 further contains a couch 33 and a couch driving unit 34. The couch 33 is supported on the base so that the couch 33 can be rotated around an X-axis, a Y-axis and a Z-axis and can be moved in parallel to the X-axis, the Y-axis and the Z-axis. The X-axis, the Y-axis and the Z-axis are orthogonal to one another. The couch 33 is used to lay a patient 35 to be treated by the radiotherapy system. The couch 33 contains a fixing tool (not shown). The fixing tool fixes the patient 35 onto the couch 33 so that the patient 35 does not move. The couch driving unit 34 is controlled by the control unit 10 and moves the couch 33 rotationally and parallelly.

Figure 3:
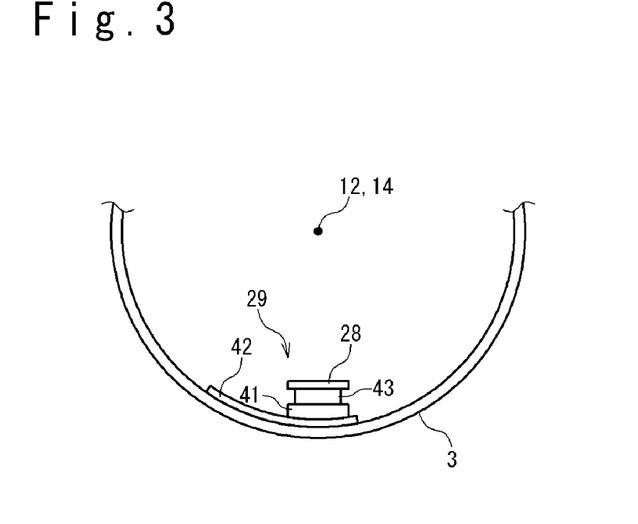
FIG. 3 is a plan view showing an imager driving unit.

FIG. 3 shows the imager driving unit 29. The imager driving unit 29 contains a frame 41, a circumferential direction driving unit 42 and a radial direction driving unit 43. The frame 41 is supported by the running gantry 3 so that the frame 41 can be turned around the gantry rotation axis 12. At this time, the second imaging unit 28 is supported by the frame 41 so that the second imaging unit 28 can be moved in parallel to a radial direction and can be turned. The radial direction is orthogonal to the gantry rotation axis 12 and parallel to a line linking the center of the light receiving section of the second imaging unit 28 and the isocenter 14. The circumferential direction driving unit 42 is controlled by the control unit 10 and makes the frame 41 turn around the gantry rotation axis 12 with respect to the running gantry 3. The radial direction driving unit 43 is controlled by the control unit 10 and drives the second imaging unit 28 to move in parallel toward the isocenter 14 with respect to the frame 41.

For this reason, the imager driving unit 29 can move the second imaging unit 28, while the light receiving section of the second imaging unit 28 is oriented to the isocenter 14.

Figure 4:
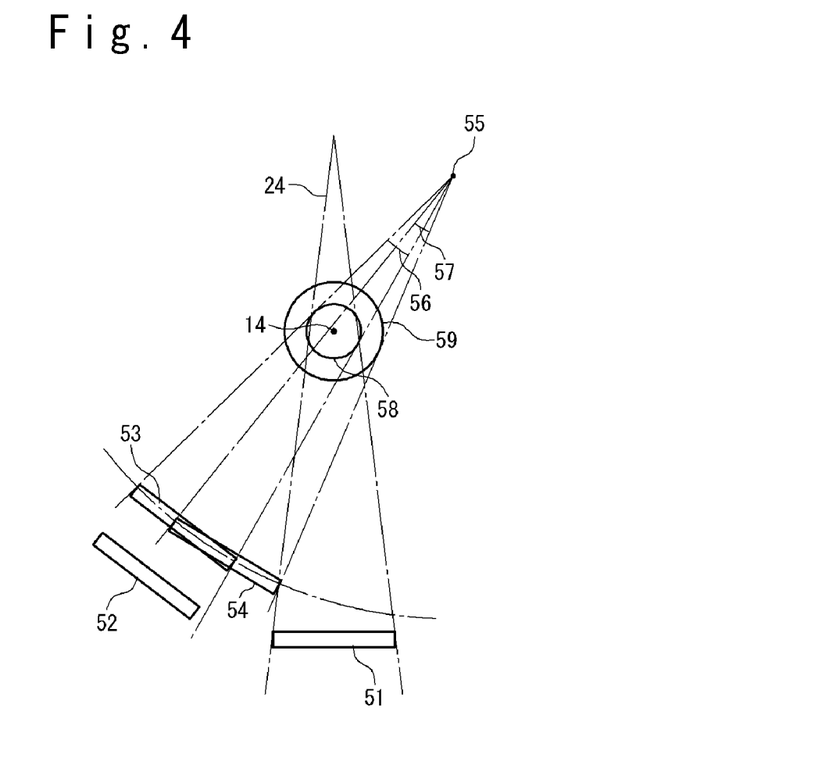
FIG. 4 is a plan view showing a plurality of positions at which a second sensor array is arranged.

FIG. 4 shows a plurality of positions at which the second imaging unit 28 is positioned by the imager driving unit 29. The plurality of positions include an MV-X ray imaging position 51, an avoidance position 52, a kV-X ray imaging position 53 and a wide view field reconstruction image imaging position 54.

The MV-X ray imaging position 51 indicates a position opposite to the radiation irradiating unit 6 through the isocenter 14. That is, when the second imaging unit 28 is positioned into the MV-X ray imaging position 51, the center of the light receiving section of the second imaging unit 28, the virtual point source from which the therapeutic radiation 24 is emitted, and the isocenter 14 are located on a straight line. That is, when the second imaging unit 28 is positioned into the MV-X ray imaging position 51, it is possible to image the transmission image in which the isocenter 14 is reflected on the center by the therapeutic radiation 24 emitted from the radiation irradiating unit 6.

The avoidance position 52 indicates a position that is sufficiently away from a region which is exposed to the therapeutic radiation 24 emitted from the radiation irradiating unit 6. That is, when the second imaging unit 28 is positioned into the avoidance position 52, an exposure amount of the therapeutic radiation 24 is sufficiently small, as compared with an exposure amount of the therapeutic radiation 24 when the second imaging unit 28 is positioned into the MV-X ray imaging position 51.

The kV-X ray imaging position 53 indicates a position opposite to the second diagnostic radiation irradiating unit 26 through the isocenter 14. This position is set such that, when the second imaging unit 28 is positioned into the kV-X ray imaging position 53, the center of the light receiving section of the second imaging unit 28, the virtual point source 55 from which the second diagnostic radiation 32 is emitted, and the isocenter 14 are positioned on a straight line. That is, when the second imaging unit 28 is positioned into the MV-X ray imaging position 51, it is possible to image the transmission image in which the isocenter 14 is reflected on the center by the second diagnostic radiation 32 emitted from the second diagnostic radiation irradiating unit 26.

The wide view field reconstruction image imaging position 54 is set such that, when the second imaging unit 28 is positioned into the kV-X ray imaging position 53, a straight line linking the virtual point source 55 and the isocenter 14 intersects the end portion of the light receiving section of the second imaging unit 28. That is, when the second imaging unit 28 is positioned into the kV-X ray imaging position 53 and then moved by a predetermined angle around the gantry rotation axis 12 by the circumferential direction driving unit 42 of the imager driving unit 29, the second imaging unit 28 is positioned into the wide view field reconstruction image imaging position 54.

It should be noted that the avoidance position 52 may be same as the kV-X ray imaging position 53, when the second imaging unit 28 positioned into the kV-X ray imaging position 53 is not sufficiently exposed to the therapeutic radiation 24. Moreover, the avoidance position 52 may be also same as the wide view field reconstruction image imaging position 54, when the second imaging unit 28 positioned into the wide view field reconstruction image imaging position 54 is not sufficiently exposed to the therapeutic radiation 24.

Figure 5:
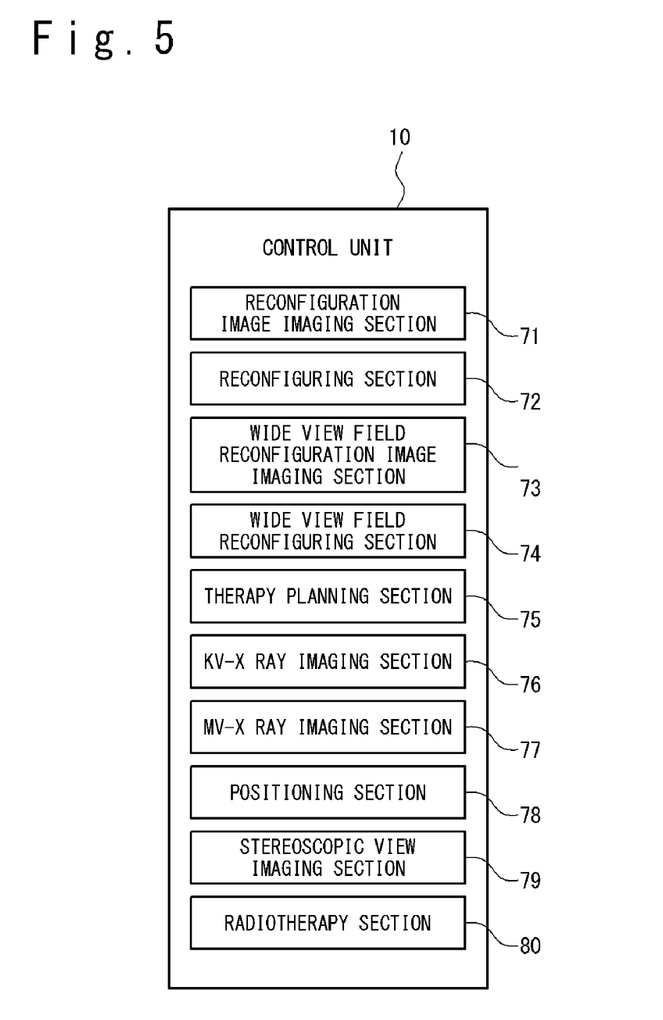
FIG. 5 is a block diagram showing a control unit of the radiotherapy apparatus.

FIG. 5 shows the control unit 10. The control unit 10 is a computer, which includes CPU, a storage unit, a removable memory drive, a communication unit, an input unit, an output unit and an interface. The CPU executes a computer program that is installed in the control unit 10 and controls the storage unit, the removable memory drive, the communication unit, the input unit, the output unit and the interface. The storage unit stores the computer program. The storage unit further stores data used by the CPU. When a recording medium in which the computer program is recorded is inserted, the removable memory drive is used when the computer program is installed in the control unit 10. The communication unit is used when the computer program is downloaded from another computer, which is connected through a communication line network to the control unit 10, to the control unit 10 and then the computer program is installed in the control unit 10. The input unit outputs data generated by the operation of a user to the CPU. As the input unit, a keyboard and a mouth are exemplified. The output unit recognizably outputs the data generated by the CPU to the user. As the output unit, a display for displaying the image generated by the CPU is exemplified.

The interface outputs data generated by an external equipment connected to the control unit 10, to the CPU and outputs the data generated by the CPU to the external equipment. The external equipment includes the radiation irradiating unit 6, the ring driving unit 21, the gantry driving unit, the gimbal unit 23, the first diagnostic radiation irradiating unit 25, the second diagnostic radiation irradiating unit 26, the first imaging unit 27, the second imaging unit 28, the imager driving unit 29 and the couch driving unit 34.

The computer program installed in the control unit 10 is provided with a plurality of computer program portions for attaining a plurality of functions by the control unit 10, respectively. The plurality of functions include a reconstruction image imaging section 71, a reconstructing section 72, a wide view field reconstruction image imaging section 73, a wide view field reconstructing section 74, a therapy planning section 75, a kV-X ray imaging section 76, an MV-X ray imaging section 77, a position adjusting section 78, a stereoscopic view imaging section 79 and a radiotherapy section 80.

The reconstruction image imaging section 71 controls the radiotherapy apparatus 1 to image a plurality of reconstruction transmission images on which a photographic subject located in the isocenter 14 is reflected. That is, the reconstruction image imaging section 71 controls the imager driving unit 29 so that the second imaging unit 28 is positioned into the kV-X ray imaging position 53. The reconstruction image imaging section 71 controls the ring driving unit 21 so that with respect to the base, the O-ring 2 is positioned into a predetermined ring angle. The reconstruction image imaging section 71 further controls the gantry driving unit so that with respect to the O-ring 2, the running gantry 3 is rotated at a constant angular speed around the gantry rotation axis 12. The reconstruction image imaging section 71 further controls the second diagnostic radiation irradiating unit 26 so that the second diagnostic radiation 32 is emitted when the running gantry 3 is positioned into a predetermined gantry angle. As the predetermined gantry angle, an arithmetic progression is exemplified in which a tolerance is 0.5 degrees and a difference between its first item and its final item is 180 degrees. The reconstruction image imaging section 71 further controls the second imaging unit 28 so that the reconstruction transmission image is imaged when the with respect to the O-ring 2, the running gantry 3 is positioned into the predetermined gantry angle.

The reconstructing section 72 reconstructs a three-dimensional data on the basis of a plurality of reconstruction images imaged by the reconstruction image imaging section 71. The three-dimensional data indicates a plurality of tomographic images or voxel data. The plurality of tomographic images correspond to a plurality of sectional planes perpendicular to the gantry rotation axis 12. In any tomographic image of the plurality of tomographic images, a plurality of CT values are related to a plurality of pixels. The plurality of pixels correspond to a plurality of regions that fill the tomographic image without a gap in an optional sectional plane of the plurality of sectional planes, respectively. For example, each of the plurality of regions is formed as a square. One CT value corresponding to an optional pixel of the plurality of CT values corresponds to a transmission coefficient (X-ray absorption coefficient) of a space near the region corresponding to the optional pixel of the plurality of regions. In the voxel data, the plurality of CT values are related to a plurality of voxels. The plurality of voxels correspond to the plurality of regions which fill a space in which the patient 35 is located, without any gap. For example, each of the plurality of regions is formed as a rectangular parallelepiped. One CT value corresponding to an optional voxel of the plurality of CT values corresponds to the transmission coefficient (X-ray absorption coefficient) corresponding to the optional voxel of the plurality of regions.

The wide view field reconstruction image imaging section 73 controls the radiotherapy apparatus 1 to image the plurality of reconstruction transmission images on which the photographic subject located in the isocenter 14 is reflected. That is, the wide view field reconstruction image imaging section 73 controls the imager driving unit 29 so that the second diagnostic radiation irradiating unit 26 is positioned into the wide view field reconstruction image imaging position 54. The wide view field reconstruction image imaging section 73 controls the ring driving unit 21 so that with respect to the base, the O-ring 2 is positioned into the predetermined ring angle. The wide view field reconstruction image imaging section 73 further controls the gantry driving unit so that with respect to the O-ring 2, the running gantry 3 is rotated at a constant angular speed around the gantry rotation axis 12. The wide view field reconstruction image imaging section 73 further controls the second diagnostic radiation irradiating unit 26 so that the second diagnostic radiation 32 is emitted when the running gantry 3 is positioned into the predetermined gantry angle. As the predetermined gantry angle, a mathematic progression is exemplified in which a tolerance is 0.5 degrees and a difference between the initial item and the final item is 360 degrees. The wide view field reconstruction image imaging section 73 further controls the second imaging unit 28 so that the reconstruction transmission image is imaged when with respect to the O-ring 2, the running gantry 3 is positioned into a predetermined gantry angle.

The wide view field reconstructing section 74 reconstructs three-dimensional data on the basis of the plurality of reconstruction images imaged by the wide view field reconstruction image imaging section 73. The three-dimensional data indicates the plurality of tomographic images or voxel data, similarly to the three-dimensional data reconstructed by the wide view field reconstructing section 74.

The therapy planning section 75 displays the three-dimensional data reconstructed by the reconstructing section 72 on the display or displays the three-dimensional data reconstructed by the wide view field reconstructing section 74 on the display. The therapy planning section 75 further collects data related to a therapy plan from the input unit. The therapy plan is prepared on the basis of the three-dimensional data and indicates combinations of an irradiation angle and a dose. The irradiation angle indicates a direction in which the therapeutic radiation 24 is irradiated to the affected region of the patient 35, and also indicates the ring angle and the gantry angle. The ring angle indicates the position of the O-ring 2 with respect to the base. The gantry angle indicates the position of the running gantry 3 with respect to the O-ring 2. The dose indicates a dose of the therapeutic radiation 24 that is irradiated to the patient 35 in the irradiation angle.

The kV-X ray imaging section 76 controls the radiotherapy apparatus 1 so that a first kV-X ray transmission image and a second kV-X ray transmission image are imaged in which the photographic subject located in the isocenter 14 is reflected. That is, the kV-X ray imaging section 76 controls the ring driving unit 21 so that with respect to the base, the O-ring 2 is positioned into a predetermined ring angle. The kV-X ray imaging section 76 further controls the gantry driving unit so that with respect to the O-ring 2, the running gantry 3 is positioned into a predetermined gantry angle. The kV-X ray imaging section 76 controls the imager driving unit 29 so that the second imaging unit 28 is positioned into the kV-X ray imaging position 53.

Next, the kV-X ray imaging section 76 controls the first diagnostic radiation irradiating unit 25 so that the first diagnostic radiation 31 is emitted. The kV-X ray imaging section 76 controls the first imaging unit 27 so that the first kV-X ray transmission image is imaged. The kV-X ray imaging section 76 controls the second diagnostic radiation irradiating unit 26 so that the second diagnostic radiation 32 is emitted. The kV-X ray imaging section 76 controls the second imaging unit 28 so that the second kV-X ray transmission image is imaged.

The MV-X ray imaging section 77 controls the radiotherapy apparatus 1 so that an MV-X ray transmission image in which the photographic subject located in the isocenter 14 is reflected is imaged. That is, the MV-X ray imaging section 77 controls the ring driving unit 21 so that with respect to the base, the O-ring 2 is positioned into a predetermined ring angle. The MV-X ray imaging section 77 further controls the gantry driving unit so that with respect to the O-ring 2, the running gantry 3 is positioned into a predetermined gantry angle. The MV-X ray imaging section 77 controls the imager driving unit 29 so that the second imaging unit 28 is positioned into the MV-X ray imaging position 51. Next, the MV-X ray imaging section 77 controls the radiation irradiating unit 6 so that the therapeutic radiation 24 is emitted. The MV-X ray imaging section 77 controls the second imaging unit 28 so that the MV-X ray transmission image is imaged.

The positioning section 78 calculates a patient displacement amount on the basis of the three-dimensional data used by the therapy planning section 75 and the first kV-X ray transmission image and the second kV-X ray transmission image, which are imaged by the kV-X ray imaging section 76. The three-dimensional data is the three-dimensional data reconstructed by the reconstructing section 72 or the three-dimensional data reconstructed by the wide view field reconstructing section 74. When the position of the patient 35 indicated by the first kV-X ray transmission image and the second kV-X ray transmission image is displaced from the position of the patient 35 indicated by the three-dimensional data, a patient displacement amount indicates a kind and degree of the displacement. The positioning section 78 controls the couch driving unit 34 so that the patient 35 is positioned into the position of the patient 35 indicated by the three-dimensional data on the basis of the patient displacement amount.

The positioning section 78 further calculates a displacement amount of the radiation irradiating unit on the basis of the MV-X ray transmission image imaged by the MV-X ray imaging section 77. When the position of the therapeutic radiation 24 is displaced from the position of the affected region of the patient 35, the displacement amount of the radiation irradiating unit indicates a degree of the displacement of the radiation irradiating unit. The positioning section 78 controls the gimbal unit 23 so that the therapeutic radiation 24 is emitted toward a predetermined position on the basis of the displacement amount of the radiation irradiating unit.

The stereoscopic view imaging section 79 controls the radiotherapy apparatus 1 so that a first tracking transmission image and a second tracking transmission image in which the affected region of the patient 35 is reflected are imaged. That is, the stereoscopic view imaging section 79 controls the ring driving unit 21 so that with respect to the base, the O-ring 2 is positioned into a predetermined ring angle. The predetermined ring angle indicates a ring angle that is indicated by a therapy plan generated by the therapy planning section 75. The stereoscopic view imaging section 79 further controls the gantry driving unit so that with respect to the O-ring 2, the running gantry 3 is positioned into a predetermined gantry angle. The predetermined gantry angle indicates a gantry angle that is indicated by the therapy plan generated by the therapy planning section 75. The stereoscopic view imaging section 79 controls the imager driving unit 29 so that the second imaging unit 28 is positioned into the kV-X ray imaging position 53.

Next, the stereoscopic view imaging section 79 controls the first diagnostic radiation irradiating unit 25 so that the first diagnostic radiation 31 is emitted. The stereoscopic view imaging section 79 controls the first imaging unit 27 so that the first tracking transmission image is imaged. The stereoscopic view imaging section 79 controls the second diagnostic radiation irradiating unit 26 so that the second diagnostic radiation 32 is emitted. The stereoscopic view imaging section 79 controls the second imaging unit 28 so that the second tracking transmission image is imaged.

The radiotherapy unit 80 calculates the position of the affected region of the patient 35 on the basis of the first tracking transmission image and the second tracking transmission image which are imaged by the stereoscopic view imaging section 79. The radiotherapy unit 80 further controls the gimbal unit 23 so that the therapeutic radiation 24 is emitted toward the affected region.

The radiotherapy apparatus controlling method according to an embodiment of the present invention is executed by the control unit 10 and contains an operation of generating narrow view field three-dimensional data, an operation of generating wide view field three-dimensional data, an operation of generating the therapy plan, an operation of positioning the patient, and an operation of carrying out the radiotherapy.

The operation of generating the narrow view field three-dimensional data firstly controls the couch driving unit 34 so that with respect to the base, the couch 33 is positioned into a predetermined position, after the patient 35 is fixed to the couch 33. The control unit 10 further controls the imager driving unit 29 so that the second imaging unit 28 is positioned into the kV-X ray imaging position 53. The control unit 10 controls the ring driving unit 21 so that with respect to the base, the O-ring 2 is positioned into a predetermined ring angle. The control unit 10 further controls the gantry driving unit so that with respect to the O-ring 2, the running gantry 3 is rotated around the gantry rotation axis 12 in a constant angular velocity. The control unit 10 further controls the second diagnostic radiation irradiating unit 26 so that the second diagnostic radiation 32 is emitted when the running gantry 3 is positioned into the predetermined gantry angle. The predetermined gantry angle is represented as a mathematic progression in which a tolerance is 0.5 degrees and a difference between its first item and its final item is 180 degrees. The control unit 10 further controls the second imaging unit 28 so that the reconstruction transmission image is imaged when with respect to the O-ring 2, the running gantry 3 is positioned into the predetermined gantry angle. The control unit 10 reconstructs the narrow view field three-dimensional data on the basis of the plurality of reconstruction images.

The operation of generating the wide view field three-dimensional data firstly controls the couch driving unit 34 so that with respect to the base, the couch 33 is positioned into a predetermined position, after the patient 35 is fixed to the couch 33. The control unit 10 further controls the imager driving unit 29 so that the second diagnostic radiation irradiating unit 26 is positioned into the wide view field reconstruction image imaging position 54. The control unit 10 controls the ring driving unit 21 so that with respect to the base, the O-ring 2 is positioned into a predetermined ring angle. The control unit 10 further controls the gantry driving unit so that with respect to the O-ring 2, the running gantry 3 is rotated around the gantry rotation axis 12 at a constant angular velocity. The control unit 10 further controls the second diagnostic radiation irradiating unit 26 so that the second diagnostic radiation 32 is emitted when the running gantry 3 is positioned into the predetermined gantry angle. The predetermined gantry angle is represented as a mathematic progression in which a tolerance is 0.5 degrees and a difference between its first item and its final item is 360 degrees. The control unit 10 further controls the second imaging unit 28 so that the reconstruction transmission image is imaged when with respect to the O-ring 2, the running gantry 3 is positioned into the predetermined gantry angle. The control unit 10 reconstructs the wide view field three-dimensional data on the basis of the plurality of reconstruction images.

A view field 56 of the reconstruction transmission image imaged by the second imaging unit 28 when the second imaging unit 28 is positioned into the kV-X ray imaging position 53 is set such that as shown in FIG. 4, the gantry rotation axis 12 is reflected on the center of the reconstruction transmission image. A region 58 indicated by the three-dimensional data obtained by reconstructing the plurality of reconstruction transmission images imaged by the second imaging unit 28 when the second imaging unit 28 is positioned into the wide view field reconstruction image imaging position 54 shows a rotation body obtained when a predetermined figure is rotated around the gantry rotation axis 12.

A view field 57 of the reconstruction transmission image imaged by the second imaging unit 28 when the second imaging unit 28 is positioned into the wide view field reconstruction image imaging position 54 is set such that as shown in FIG. 4, the gantry rotation axis 12 is reflected at the end of the reconstruction transmission image. A region 59 indicated by the three-dimensional data obtained by reconstructing the plurality of reconstruction transmission images imaged by the second imaging unit 28 when the second imaging unit 28 is positioned into the wide view field reconstruction image imaging position 54 shows a rotation body obtained when a predetermined figure is rotated around the gantry rotation axis 12. At this time, the region 59 is larger in volume than the region 58. That is, the radiotherapy apparatus 1 can image the reconstruction transmission image necessary to reconstruct the three-dimensional data of the region 58 and the reconstruction transmission image necessary to reconstruct the three-dimensional data of the region 59 by using the single second diagnostic radiation irradiating unit 26 and the single second imaging unit 28.

Moreover, according to the above radiotherapy apparatus controlling method, the number of reconstruction transmission images necessary to reconstruct the three-dimensional data of the region 59 is larger than the number of reconstruction transmission images necessary to reconstruct the three-dimensional data of the region 58. For this reason, a time required to image the reconstruction transmission images that are necessary to reconstruct the three-dimensional data of the region 59 is longer than a time required to image the reconstruction transmission images that are necessary to reconstruct the three-dimensional data of the region 58. Moreover, a dose of the second diagnostic radiation 32 that is irradiated to the patient 35 when the reconstruction transmission images necessary to reconstruct the three-dimensional data of the region 59 are imaged is greater than a dose of the second diagnostic radiation 32 irradiated to the patient 35 when the reconstruction transmission images necessary to reconstruct the three-dimensional data of the region 58 is imaged.

That is, according to the above radiotherapy apparatus 1, when it is desired to acquire the three-dimensional data of a wide region of the patient 35, a user instructs the control unit 10 to execute the operation of generating the wide view field three-dimensional data. When it is desired to image the reconstruction transmission images necessary to reconstruct the three-dimensional data at a higher speed, or when it is desired to reduce a dose of the patient 35, the user instructs the control unit 10 to execute the operation of generating the narrow view field three-dimensional data. That is, according to the above radiotherapy apparatus 1, the user can properly select and acquire the three-dimensional data that indicates a suitable region of the region 58 and the region 59.

A technique that changes the size of the view field of the three-dimensional data by changing the position of the view field of the plurality of transmission images imaged to reconstruct the three-dimensional data is known and disclosed in, for example, JP 2003-522576A.

The operation of generating the therapy plan is executed after the execution of the operation of generating the narrow view field three-dimensional data or after the execution of the operation of generating the wide view field three-dimensional data. The control unit 10 displays the reconstructed three-dimensional data on a display unit, or displays the three-dimensional data reconstructed by the wide view field reconstructing section 74 on the display. The user prepares the therapy plan on the basis of the three-dimensional data. The therapy plan indicates combinations of an irradiation angle and a dose. The irradiation angle indicates an irradiation direction when the therapeutic radiation 24 is irradiated to the affected region of the patient 35 and includes a ring angle and a gantry angle. The ring angle indicates a position of the O-ring 2 with respect to the base. The gantry angle indicates a position of the running gantry 3 with respect to the O-ring 2. The dose indicates a dose of the therapeutic radiation 24 that is irradiated to the patient 35 at the irradiation angle. The user inputs the therapy plan to the control unit 10 through the input unit of the control unit 10.

The operation of positioning the patient is executed after the execution of the operation of generating the therapy plan of the patient, for example, several days after the execution of the operation of generating the therapy plan. The control unit 10 firstly controls the couch driving unit 34 so that with respect to the base, the couch 33 is positioned into a predetermined position after the patient 35 is fixed to the couch 33. The control unit 10 further controls the imager driving unit 29 so that the second imaging unit 28 is positioned into the kV-X ray imaging position 53. The control unit 10 controls the ring driving unit 21 so that the O-ring 2 is positioned into the ring angle indicated by the therapy plan with respect to the base. The control unit 10 further controls the gantry driving unit of the radiotherapy apparatus 1 so that the running gantry 3 is positioned into the gantry angle indicated by the therapy plan.

The control unit 10 controls the first diagnostic radiation irradiating unit 25 so that the first diagnostic radiation 31 is emitted after the radiation irradiating unit 6 is positioned into the predetermined position to the patient 35, and controls the first imaging unit 27 so that the first kV-X ray transmission image is imaged. The control unit 10 further controls the second diagnostic radiation irradiating unit 26 so that the second diagnostic radiation 32 is emitted after the radiation irradiating unit 6 is positioned into the predetermined position to the patient 35, and controls the second imaging unit 28 so that the second kV-X ray transmission image is imaged.

The control unit 10 calculates the patient displacement amount on the basis of the three-dimensional data, the first kV-X ray transmission image and the second kV-X ray transmission image. The control unit 10 controls the couch driving unit 34 so that the patient 35 is positioned into the position indicated by the three-dimensional data on the basis of the patient displacement amount. The control unit 10 repeatedly executes the imaging of the first kV-X ray transmission image and the second kV-X ray transmission image and the moving of the patient 35, until the patient displacement amount becomes smaller than a predetermined value.

The control unit 10 controls the imager driving unit 29 so that the second imaging unit 28 is positioned into the MV-X ray imaging position 51, after the patient 35 is positioned into the position indicated by the three-dimensional data. Next, the control unit 10 controls the radiation irradiating unit 6 so that the therapeutic radiation 24 is emitted. The control unit 10 controls the second imaging unit 28 so that the MV-X ray transmission image is imaged. The control unit 10 calculates the displacement amount of the radiation irradiating unit on the basis of the MV-X ray transmission image. The displacement amount of the radiation irradiating unit indicates a degree by which the irradiation position of the therapeutic radiation 24 displaces from the position of the affected region of the patient 35. The control unit 10 controls the gimbal unit 23 so that the therapeutic radiation 24 is irradiated to a predetermined region on the basis of the displacement amount of the radiation irradiating unit.

That is, the radiotherapy apparatus 1 can image the kV-X ray transmission image and the MV-X ray transmission image by using the single second diagnostic radiation irradiating unit 26 and the single second imaging unit 28. At this time, the radiotherapy apparatus 1 can be manufactured at cheaper cost, as compared with another radiotherapy apparatus in which the imaging unit for receiving the therapeutic radiation 24 and the imaging unit for receiving the second diagnostic radiation 32 are separately provided.

The operation of carrying out the radiotherapy is performed after carrying out the operation of positioning the patient. The control unit 10 controls the imager driving unit 29 so that the second imaging unit 28 is positioned into the kV-X ray imaging position 53, after the radiation irradiating unit 6 is positioned into a predetermined position to the patient 35. The control unit 10 controls the first diagnostic radiation irradiating unit 25 and the first imaging unit 27 so that the first tracking transmission image of the patient 35 is imaged, after the radiation irradiating unit 6 is positioned into a predetermined position to the patient 35, and controls the second diagnostic radiation irradiating unit 26 and the second imaging unit 28 so that the second tracking transmission image of the patient 35 is imaged.

The control unit 10 calculates the position and shape of the affected region of the patient 35 on the basis of the first tracking transmission image and the second tracking transmission image. The control unit 10 controls the gimbal unit 23 so that the radiation irradiating unit 6 is oriented to the calculated position. The control unit 10 controls the radiation irradiating unit 6 so that the irradiation field of the therapeutic radiation 24 coincides with the shape of the affected region and also the therapeutic radiation 24 of a predetermined dose is irradiated to the affected region. Moreover, the control unit 10 periodically repeats the operations from the imaging of the tracking transmission image to the irradiation of the therapeutic radiation 24, until the therapeutic radiation 24 of the dose indicated by the therapy plan is irradiated to the affected region of the patient 35.

According to the above radiotherapy, even if the affected region of the patient 35 moves, the control unit 10 can irradiate the therapeutic radiation 24 to the affected region at a higher precision and can perform the radiotherapy on the patient 35 at a higher precision.

Moreover, according to the above radiotherapy, as compared with the therapy in which the therapeutic radiation 24 is emitted to the patient 35 in the situation that the second imaging unit 28 is positioned into the MV-X ray imaging position 51, a dose of the therapeutic radiation 24 to which the second imaging unit 28 is exposed can be further reduced, which can extend the life of the second imaging unit 28.

It should be noted that in the operation of performing the radiotherapy, the control unit 10 may also calculate the position and shape of the affected region of the patient 35 on the basis of a surrogate value measured by another sensor that differs from the second imaging unit 28, without imaging the second tracking transmission image. As the other sensor, an infrared camera is exemplified which reflects the image of a marker attached to the patient 35. At this time, as the surrogate value, a position at which the marker is reflected on the image is exemplified. At this time, after controlling the imager driving unit 29 so that the second imaging unit 28 is positioned into the avoidance position 52, the control unit 10 controls the gimbal unit 23 so that the radiation irradiating unit 6 is oriented to the calculated region, and then controls the radiation irradiating unit 6 so that the therapeutic radiation 24 is irradiated to the affected region.

The above radiotherapy can reduce the dose of the therapeutic radiation 24 exposed to the second imaging unit 28, as compared with the fact that the therapeutic radiation 24 is emitted to the patient 35 in the situation in which the second imaging unit 28 is positioned into the MV-X ray imaging position 51, similarly to the radiotherapy in the above-mentioned embodiment, and can extend the life of the second imaging unit 28.

Figure 6:
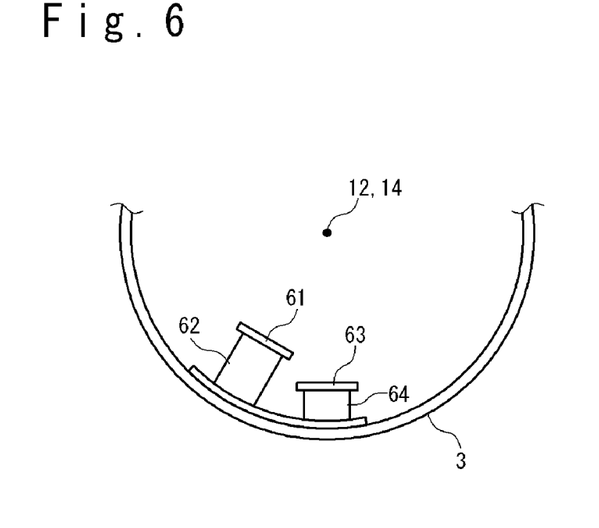
FIG. 6 is a plan view showing another radiotherapy apparatus.

FIG. 6 shows another radiotherapy apparatus. In its radiotherapy apparatus, the second imaging unit 28 and the imager driving unit 29 in the radiotherapy apparatus 1 in the above-mentioned embodiment are replaced with a kV-X ray imaging unit 61, a first imager driving unit 62, an MV-X ray imaging unit 63 and a second imager driving unit 64. The first imager driving unit 62 is controlled by the control unit 10 such that the kV-X ray imaging unit 61 is positioned into one of the kV-X ray imaging position 53 and the wide view field reconstruction image imaging position 54. The kV-X ray imaging unit 61 is controlled by the control unit 10 to generate the transmission image on the basis of the X-ray received by the light receiving section. The second imaging driving unit 64 positions the MV-X ray imaging unit 63 in one of the MV-X ray imaging position 51 and the avoidance position 52. The MV-X ray imaging unit 63 is controlled by the control unit 10 to generate the transmission image on the basis of the X-ray received by the light receiving section.

When reconstructing the three-dimensional data of the region 58, the control unit 10 firstly controls the first imager driving unit 62 so that the kV-X ray imaging unit 61 is positioned into the kV-X ray imaging position 53. The control unit 10 further controls the second diagnostic radiation irradiating unit 26 so that the second diagnostic radiation 32 is emitted, when the running gantry 3 is positioned into a predetermined gantry angle. The predetermined gantry angle is represented as a mathematic progression in which the tolerance is 0.5 degrees and the difference between the first item and the final item is 180 degrees. The control unit 10 further controls the kV-X ray imaging unit 61 so that the reconstruction transmission image is imaged, when with respect to the O-ring 2, the running gantry 3 is positioned into a predetermined gantry angle. The control unit 10 reconstructs the three-dimensional data of the region 58 on the basis of the plurality of reconstruction transmission images.

When reconstructing the three-dimensional data of the region 59, the control unit 10 firstly controls the first imager driving unit 62 so that the kV-X ray imaging unit 61 is positioned into the wide view field reconstruction image imaging position 54. The control unit 10 further controls the second diagnostic radiation irradiating unit 26 so that the second diagnostic radiation 32 is emitted when the running gantry 3 is positioned into a predetermined gantry angle. The predetermined gantry angle is represented as a mathematic progression in which the tolerance is 0.5 degrees and the difference between the first item and the final item is 360 degrees. The control unit 10 further controls the kV-X ray imaging unit 61 so that the reconstruction transmission image is imaged when with respect to the O-ring 2, the running gantry 3 is positioned into the predetermined gantry angle. The control unit 10 reconstructs the three-dimensional data of the region 59 on the basis of the plurality of reconstruction transmission images.

The control unit 10 firstly controls the second imager driving unit 64 so that the MV-X ray imaging unit 63 is positioned into the MV-X ray imaging position 51, when the transmission image is imaged from the therapeutic radiation 24, for example, in order to confirm whether or not the radiation irradiating unit 6 is oriented to a predetermined direction. After the MV-X ray imaging unit 63 is positioned into the MV-X ray imaging position 51, the control unit 10 controls the radiation irradiating unit 6 so that the therapeutic radiation 24 is irradiated, and controls the MV-X ray imaging unit 63 so that the transmission image is imaged.

When performing the radiotherapy, the control unit 10 firstly controls the second imager driving unit 64 so that the MV-X ray imaging unit 63 is positioned into the avoidance position 52. After the MV-X ray imaging unit 63 is positioned into the avoidance position 52, the control unit 10 controls the radiation irradiating unit 6 so that the therapeutic radiation 24 is emitted to the patient 35.

According to the above radiotherapy apparatus, the user can properly select and acquire the three-dimensional data that indicates a suitable region of the region 58 and the region 59, by using the control unit 10.

According to the above radiotherapy apparatus, the control unit 10 can further reduce the dose of the therapeutic radiation 24 irradiated to the MV-X ray imaging unit 63 and can extend the life of the MV-X ray imaging unit 63.

It should be noted that this application claims a priority based on Japan Patent Application No. JP 2010-189754 filed on Aug. 26, 2010, and the disclosure thereof is incorporated herein by reference.

The invention claimed is:

1. A control unit of a radiotherapy apparatus, comprising:
a first imaging section configured to control an imager driving unit to move an imaging unit along a circumferential direction of a ring-shaped gantry such that said imaging unit is positioned into a first position arranged inside of said ring-shaped gantry; and
a second imaging section configured to control said imager driving unit such that said imaging unit is positioned into a second position arranged inside of said ring-shaped gantry,
wherein said imaging unit:
receives, when said imaging unit is positioned into the first position, a first transmission radiation, which has passed a predetermined region, of a first radiation emitted from a first irradiating unit supported by said ring-shaped gantry, and images a first transmission image from the first transmission radiation, and
receives, when said imaging unit is positioned into the second position, a second transmission radiation, which has passed the predetermined region, of a second radiation emitted from a second irradiating unit supported by said ring-shaped gantry, and images a second transmission image from the second transmission radiation,
said control unit further comprising:
a first reconstruction image imaging section configured to control said imager driving unit to move said imaging unit such that said imaging unit is positioned into a first reorganization position with respect to said ring-shaped gantry;
a first reconstructing section configured to configure first three-dimensional data based on a plurality of said first transmission images imaged from the first radiation by said imaging unit when said imaging unit is positioned into the first reconstruction position;
a second reconstruction image imaging section configured to control said imager driving unit to move said imaging unit such that said imaging unit is positioned into a second reconstruction position with respect to said ring-shaped gantry; and
a second reconstructing section configured to reconstruct second three-dimensional data based on a plurality of said second transmission images imaged by said imaging unit when said imaging unit is positioned into the second reconstruction position,
wherein said ring-shaped gantry rotates around a rotation axis of said ring-shaped gantry,
wherein the plurality of said first transmission images are first reconstruction transmission images imaged when said ring-shaped gantry is positioned into a plurality of first gantry angles different from each other with respect to said ring-shaped gantry,
wherein the plurality of said second transmission images are second reconstruction transmission images imaged when said ring-shaped gantry is positioned into a plurality of second gantry angles different from each other with respect to said ring-shaped gantry, and
wherein a position in which said rotation axis is reflected on the plurality of first reconstruction transmission images is different from a position in which said rotation axis is reflected on the plurality of second reconstruction transmission images.

2. The control unit according to claim 1, wherein said imager driving unit comprises:
a circumferential direction driving unit configured to drive said imaging unit to turn around said rotation axis of said ring-shaped gantry; and
a radial direction driving unit configured to drive said imaging unit to move in parallel to a radial direction orthogonal to said rotation axis of said ring-shaped gantry.

3. The control unit according to claim 2, further comprising a radiotherapy section configured to control said second irradiating unit to irradiate a therapeutic radiation to a specimen,
wherein said radiotherapy section controls said imager driving unit such that said imaging unit is positioned into an avoidance position, when the therapeutic radiation is irradiated to the specimen, and
wherein a dose of the therapeutic radiation to which said imaging unit is exposed when said imaging unit is positioned into the avoidance position is smaller than a dose of the therapeutic radiation to which said imaging unit is exposed when said imaging unit is positioned into the second position.

4. The control unit according to claim 3, further comprising a stereoscopic view imaging section configured to control another imaging unit supported by said ring-shaped gantry such that a third transmission image is imaged from a radiation portion which has transmitted through the predetermined region, of a radiation emitted from a third irradiating unit supported by said ring-shaped gantry,
wherein said radiotherapy section controls a gimbal unit which moves said second irradiating unit with respect to said ring-shaped gantry, based on a first stereoscopic view image imaged by said imaging unit when said imaging unit is positioned into the first position, and a second stereoscopic view image imaged by said another imaging unit.

5. A radiotherapy apparatus controlling method comprising:

controlling an imager driving unit to move an imaging unit along a circumferential direction of a ring-shaped gantry, such that said imaging unit which images a transmission image by receiving a radiation is positioned into a first position arranged inside of said ring-shaped gantry, before a first radiation is emitted from a first irradiating unit supported by said ring-shaped gantry;

controlling said imager driving unit such that said imaging unit is positioned into a second position arranged inside of said ring-shaped gantry, before a second radiation is emitted from a second irradiating unit supported by said ring-shaped gantry;

rotating said ring-shaped gantry around a rotation axis of said ring-shaped gantry;

controlling said imager driving unit to drive said imaging unit to be positioned into a first reconstruction position with respect to said ring-shaped gantry;

reconstructing first three-dimensional data based on a plurality of first reconstruction transmission images imaged from a radiation emitted from said first irradiating unit when said imaging unit is positioned into a first reconstruction position;

controlling said imager driving unit to drive said imaging unit to be positioned into a second reconstruction position with respect to said ring-shaped gantry; and reconstructing second three-dimensional data based on a plurality of second reconstruction transmission images imaged from the radiation emitted from said second irradiating unit when said imaging unit is positioned into the second reconstruction position, wherein a first transmission radiation of the first radiation which has transmitted through a predetermined region is received by said imaging unit when said imaging unit is positioned into the first position, wherein a second transmission radiation of the second radiation which has transmitted through the predetermined region is received by said imaging unit when said imaging unit is positioned into the second position, wherein the plurality of first reconstruction transmission images are images imaged when said ring-shaped gantry is positioned into a plurality of first gantry angles different from each other with respect to said ring-shaped gantry, wherein the plurality of second reconstruction transmission images are images imaged when said ring-shaped gantry is positioned into a plurality of second gantry angles different from each other with respect to said ring-shaped gantry, and wherein a position on which said rotation axis is reflected on the plurality of first reconstruction transmission images is different from a position on which said rotation axis is reflected on the plurality of second reconstruction transmission images.

6. The radiotherapy apparatus controlling method according to claim 5, wherein said imager driving unit comprises:
a circumferential direction driving unit configured to drive said imaging unit to turn around said rotation axis of said ring-shaped gantry; and
a radial direction driving unit configured to drive said imaging unit to move in parallel to a radial direction which is orthogonal to said rotation axis of said ring-shaped gantry.

7. The radiotherapy apparatus controlling method according to claim 6, further comprising: controlling said imager driving unit to move said imaging unit to an avoidance position with respect to said ring-shaped gantry, before said second irradiating unit irradiates a therapeutic radiation, wherein a dose of the therapeutic radiation to which said imaging unit is exposed when said imaging unit is positioned into the avoidance position is smaller than a dose of the therapeutic radiation to which said imaging unit is exposed when said imaging unit is positioned into the second position.

8. The radiotherapy apparatus controlling method according to claim 7, further comprising:
calculating an irradiation position based on a first stereoscopic view image and a second stereoscopic view image; and
controlling a gimbal unit which moves said second irradiating unit with respect to said ring-shaped gantry, based on the irradiation position, before the therapeutic radiation is irradiated,
wherein said ring-shaped gantry further supports:
a third irradiating unit configured to irradiate a third radiation; and
another imaging unit configured to image a transmission image by receiving that which has transmitted through the predetermined region of the third radiation,
wherein the first stereoscopic view image is the transmission image imaged by said imaging unit when said imaging unit is positioned into the first position, and
wherein the second stereoscopic view image is the transmission image imaged by said another imaging unit.

9. A non-transitory computer-readable recording medium which stores a computer-executable program code to make a computer execute a radiotherapy apparatus controlling method comprising:

controlling an imager driving unit to move an imaging unit along a circumferential direction of a ring-shaped gantry, such that said imaging unit which images a transmission image by receiving a radiation is positioned into a first position arranged inside of said ring-shaped gantry, before a first radiation is emitted from a first irradiating unit supported by said ring-shaped gantry;

controlling said imager driving unit such that said imaging unit is positioned into a second position arranged inside of said ring-shaped gantry, before a second radiation is emitted from a second irradiating unit supported by said ring-shaped gantry;

rotating said ring-shaped gantry around a rotation axis of said ring-shaped gantry;

controlling said imager driving unit to drive said imaging unit to be positioned into a first reconstruction position with respect to said ring-shaped gantry;

reconstructing first three-dimensional data based on a plurality of first reconstruction transmission images imaged from a radiation emitted from said first irradiating unit when said imaging unit is positioned into a first reconstruction position;

controlling said imager driving unit to drive said imaging unit to be positioned into a second reconstruction position with respect to said ring-shaped gantry; and reconstructing second three-dimensional data based on a plurality of second reconstruction transmission images imaged from the radiation emitted from said second irradiating unit when said imaging unit is positioned into the second reconstruction position, wherein a first transmission radiation of the first radiation which has transmitted through a predetermined region is received by said imaging unit when said imaging unit is positioned into the first position, wherein a second transmission radiation of the second radiation which has transmitted through the predetermined region is received by said imaging unit when said imaging unit is positioned into the second position, wherein the plurality of first reconstruction transmission images are images imaged when said ring-shaped gantry is positioned into a plurality of first gantry angles different from each other with respect to said ring-shaped gantry, wherein the plurality of second reconstruction transmission images are images imaged when said ring-shaped gantry is positioned into a plurality of second gantry angles different from each other with respect to said ring-shaped gantry, and wherein a position on which said rotation axis is reflected on the plurality of first reconstruction transmission images is different from a position on which said rotation axis is reflected on the plurality of second reconstruction transmission images.

10. The non-transitory computer-readable recording medium according to claim 9, wherein said imager driving unit comprises:
   a circumferential direction driving unit configured to drive said imaging unit to turn around said rotation axis of said ring-shaped gantry; and
   a radial direction driving unit configured to drive said imaging unit to move in parallel to a radial direction which is orthogonal to said rotation axis of said ring-shaped gantry.

11. The non-transitory computer-readable recording medium according to claim 10, wherein the radiotherapy apparatus controlling method further comprises:
   controlling said imager driving unit to move said imaging unit to an avoidance position with respect to said ring-shaped gantry, before said second irradiating unit irradiates a therapeutic radiation, wherein a dose of the therapeutic radiation to which said imaging unit is exposed when said imaging unit is positioned into the avoidance position is smaller than a dose of the therapeutic radiation to which said imaging unit is exposed when said imaging unit is positioned into the second position.

12. The non-transitory computer-readable recording medium according to claim 11, wherein the radiotherapy apparatus controlling method further comprises:
   calculating an irradiation position based on a first stereoscopic view image and a second stereoscopic view image; and
   controlling a gimbal unit which moves said second irradiating unit with respect to said ring-shaped gantry, based on the irradiation position, before the therapeutic radiation is irradiated, wherein said ring-shaped gantry further supports:

a third irradiating unit configured to irradiate a third radiation; and another imaging unit configured to image a transmission image by receiving that which has transmitted through the predetermined region of the third radiation, wherein the first stereoscopic view image is the transmission image imaged by said imaging unit when said imaging unit is positioned into the first position, and wherein the second stereoscopic view image is the transmission image imaged by said another imaging unit.

* * * * *